US00PP15515P3

(12) United States Plant Patent
Berrocal

(10) Patent No.: US PP15,515 P3
(45) Date of Patent: Feb. 1, 2005

(54) ***DRACAENA* PLANT NAMED 'GOLDREAM'**

(50) Latin Name: *Dracaena Vand. Ex. L. fragrans*
Varietal Denomination: Goldream

(75) Inventor: Gonzalo Pinto Berrocal, San Jose (CR)

(73) Assignee: Exotica International (CR)

( * ) Notice: Subject to any disclaimer, the term of this patent is extended or adjusted under 35 U.S.C. 154(b) by 0 days.

(21) Appl. No.: 10/230,145

(22) Filed: Aug. 29, 2002

(65) Prior Publication Data

US 2004/0045070 P1 Mar. 4, 2004

(51) Int. Cl.[7] ..... A01H 5/00
(52) U.S. Cl. ..... Plt./383
(58) Field of Search ..... Plt./383

(56) References Cited

PUBLICATIONS

GTITM UPOVROM Citation for 'Goldream' as per QZ PBR 990694, May 4, 1999.*

* cited by examiner

*Primary Examiner*—Kent Bell
*Assistant Examiner*—Louanne Krawczewicz Myers
(74) *Attorney, Agent, or Firm*—Foley & Lardner, LLP

(57) ABSTRACT

A distinct *Dracaena* plant named 'Goldream' characterized by its relatively compact plant growth; average leaf length of 27 cm and average leaf width of 6 cm; distinctive leaf color with a light yellow-green to light yellow margin (RHS 154D to 6D) which is approximately 5 mm wide, a leaf center which is green (RHS 137A) and yellow-green (RHS 146A) with lighter vertical stripes (RHS 137C); rudimentary waved leaves sometimes slightly revolved laterally; and lightly ribbed, leaves.

2 Drawing Sheets

Genus and species of the plant claimed: *Dracaena Vand. Ex. L. fragrans.*
Variety denomination: Goldream.

BACKGROUND OF THE INVENTION

The present invention comprises a new and distinct cultivar of *Dracaena* plant botanically known as *Dracaena Vand. Ex. L. fragrans* and hereinafter referred to by the cultivar name 'Goldream'.

The new cultivar was selected by the inventor, Gonzalo Pinto Berrocal, in San Jose, Costa Rica, in July, 1973. The new cultivar was obtained as a natural branch mutation of an unnamed *Dracaena Vand. Ex. L. fragrans* (unpatented). As compared to its parent, the new variety differs in that the parent has green leaves, whereas 'Goldream' has yellow marginated leaves.

The new cultivar was first asexually propagated by the inventor in San Jose, Costa Rica, in July, 1973. Subsequent asexual reproduction of the new cultivar by division has demonstrated that the combination of characteristics as herein disclosed for the new cultivar are firmly fixed and retained through successive generations of asexual reproduction. The new cultivar reproduces true to type in successive generations of asexual reproduction.

BRIEF DESCRIPTION OF THE INVENTION

The following traits have been repeatedly observed and in combination distinguish 'Goldream' as a new and distinct cultivar:

1. Relatively compact plant growth;
2. Average leaf length of 27 cm and average leaf width of 6 cm;

3. Distinctive leaf color with a light yellow-green to light yellow margin (RHS 154D to 6D) which is approximately 5 mm wide,
4. A leaf center which is green (RHS 137A) and yellow-green (RHS 146A) with lighter vertical stripes (RHS 137C);
4. Rudimentary waved leaves sometimes slightly revolved laterally; and
5. Lightly ribbed, ensiform to broad ensiform-shaped leaves.

'Goldream' has not been observed under all possible environmental conditions. The phenotype on the new cultivar may vary significantly with variations in environment such as temperature, light intensity, and daylength without any change in genotype. The following observations, measurements and values describe plants grown in Berkel en Rodenrijs, The Netherlands under standard greenhouse conditions which closely approximate those generally used in horticultural practice.

In comparison with the well-known *Dracaena* cultivar *Dracaena Vand. Ex. L. fragrans* (unnamed, unpatented), 'Goldream' has yellow marginated leaves whereas the normal fragrans has green leaves.

BRIEF DESCRIPTION OF THE DRAWINGS

The accompanying photographic drawings illustrate a 4-month old plant of *Dracaena* 'Goldream' with colors being as true as possible with illustrations of this type.

The drawing at the top of sheet 1 shows a close-up view of the stem.

The drawing at the bottom of sheet 1 shows a side view of 'Goldream'.

The drawing at the top pf sheet 2 shows a top view of 'Goldream'.

The drawing on the bottom of sheet 2 shows a close-up view of the leaves.

DETAILED BOTANICAL DESCRIPTION

Color references are made to The Royal Horticultural Society Colour Chart (R.H.S.), except where general colors of ordinary significance are used. Colors are approximate as color depends on horticultural practices such as light level and fertilization rate, among others. The described plant is 4 months old, and was discovered as a sport in cultivated area in Boskoop, The Netherlands. Container size is 13 cm.

Propagation: Vegetative by tip cuttings.

General observations:

*Growing conditions.*—'Goldream' is grown in a commercial greenhouse under 20–21 degrees Celsius temperatures day and night. As with most *Dracaena* varieties, 'Goldream' does not stand direct sunlight so sun shields are closed when sunlight becomes too bright. No artificial lighting or photoperiodic treatments are conducted. Highest temperature resistance is at least 40 degrees Celsius, lowest is 5 degrees Celsius. Resistance, tolerance, and susceptibility to stresses: no particulars. Compound fertilizer is added to the soil. There are no other cultural or environmental treatments.

Plant habit:

*Growth rate.*—Approximately 2 cm per week.

*Plant vigor.*—Moderate.

*Form.*—Upright.

*Plant height.*—55 cm.

*Plant width.*—Average 50 cm.

Leaves:

*Form and size.*—Ensiform to broad ensiform, average length 27 cm, average width 6 cm, tips tilting downward.

*Texture.*—Smooth, glossy, only slightly furrowed at main vein.

*Veins.*—Parallel, main vein slightly furrowed.

*Under side color.*—Margins irregularly striped vertically (average width 5 mm) yellow; RHS 6D. Leaf center green; RHS 137B to 137C.

*Upper side color.*—Margins irregularly striped vertically (average width 5 mm) yellow-green; RHS 154D to yellow; RHS 6D. Leaf center green; RHS 137A and yellow-green (RHS 146A), with lighter vertical stripes, RHS 137C.

*Margin.*—Entire and wavy.

*Apex.*—Acuminate.

*Base.*—Sheathing.

*Texture.*—Moderately leathery.

*Number.*—Average of 12 leaves per 10 cm stem length.

Flowers: No inflorescences (and flowers) observed to date.

Stem:

*Diameter.*—1.3 cm (on young shoots), older shoots grow thicker when aging.

*Color.*—Young shoots green, between RHS 137A and 139A, old stems are green, RHS 137A and brown, RHS 199C.

*Texture.*—Young shoots are moderately leathery, no pubescence. Old stems are smooth, slightly glossy, marked with leaf scars.

Roots: Freely branching, greyed-orange, RHS 164B to 165B.

Plant disease/insect tolerance: Not more susceptible to pests and diseases than similar varieties.

Reproductive organs: No reproductive organs observed yet.

I claim:

1. A new and distinct cultivar of *Dracaena* plant named 'Goldream', as described and illustrated herein.

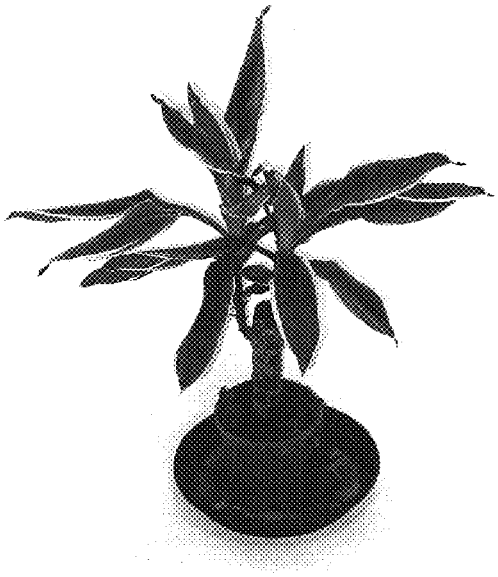
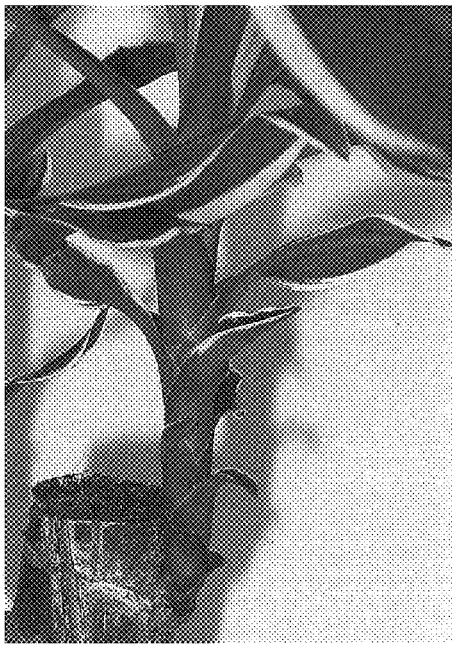

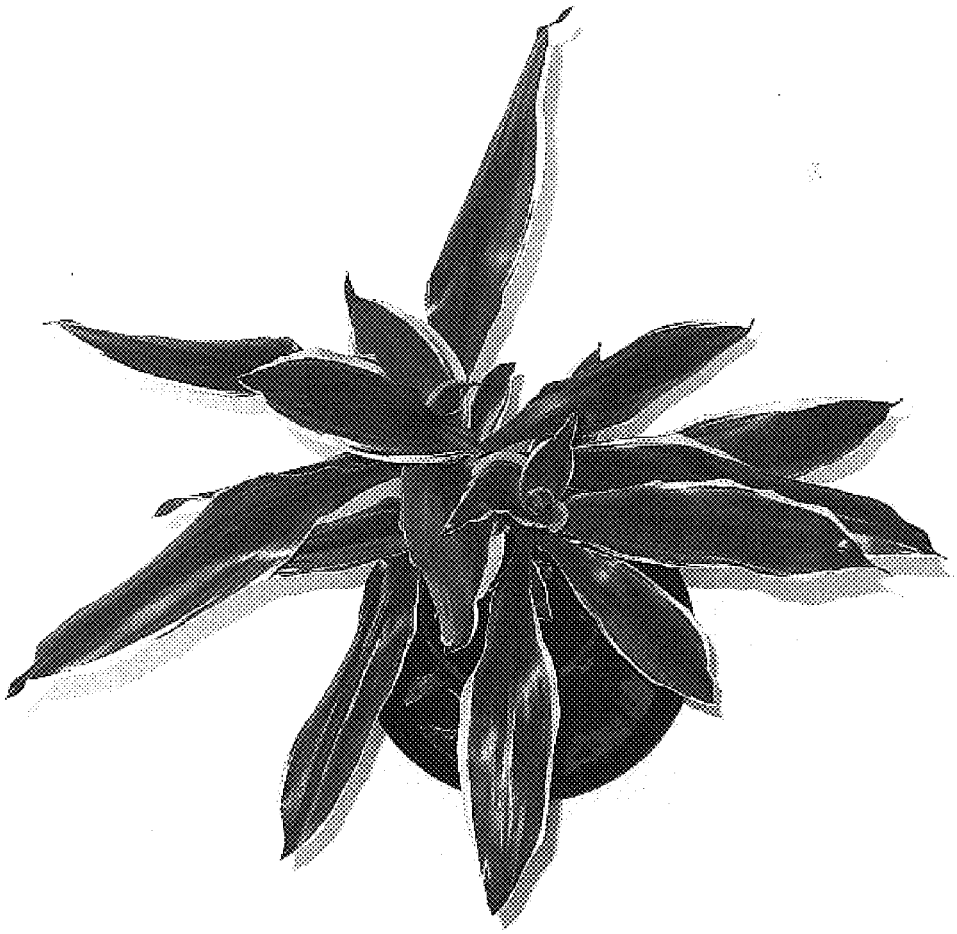
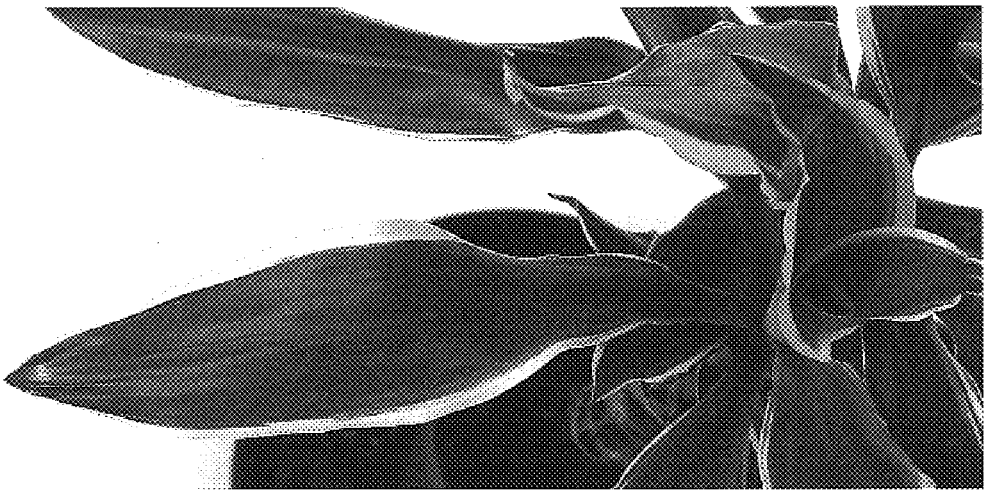

* * * * *